United States Patent
Mueller et al.

(10) Patent No.: US 8,476,418 B2
(45) Date of Patent: Jul. 2, 2013

(54) MODIFIED AAV CAPSID POLYPEPTIDES

(75) Inventors: Oliver Mueller, Heidelberg (DE); Hugo Katus, Heidelberg (DE); Karl Varadi, Heidelberg (DE); Jürgen Kleinschmidt, Bammental (DE)

(73) Assignees: Deutsches Krebsforschungszentrum, Heidelberg (DE); Ruprecht-Karls-Universitat Heidelberg, Heidelberg (DE)

( * ) Notice: Subject to any disclaimer, the term of this patent is extended or adjusted under 35 U.S.C. 154(b) by 0 days.

(21) Appl. No.: 13/322,121

(22) PCT Filed: May 28, 2010

(86) PCT No.: PCT/EP2010/057370
§ 371 (c)(1),
(2), (4) Date: Mar. 6, 2012

(87) PCT Pub. No.: WO2010/136549
PCT Pub. Date: Dec. 2, 2010

(65) Prior Publication Data
US 2012/0202732 A1 Aug. 9, 2012

(30) Foreign Application Priority Data
May 28, 2009 (EP) .................................... 09161375

(51) Int. Cl.
*A61K 38/02* (2006.01)
*A61K 9/50* (2006.01)
(52) U.S. Cl.
CPC .................................. *A61K 9/5068* (2013.01)
USPC ...................... 536/23.1; 530/387.1
(58) Field of Classification Search
None
See application file for complete search history.

(56) References Cited

U.S. PATENT DOCUMENTS
2007/0172460 A1 7/2007 Kleinschmidt

FOREIGN PATENT DOCUMENTS
WO WO 2008/145401 12/2008

OTHER PUBLICATIONS

International Search Report cited in related International Patent Application No. PCT/EP2010/057370, completed Dec. 16, 2010.
International Preliminary Report on Patentability cited in related International Patent Application No. PCT/EP2010/057370, mailed Aug. 4, 2011.
Smith et al., "Gene Therapy: Recombinant Adeno-Associated Virus Vectors," *Gene Therapy for Cardiovascular Disorders*, pp. 43-49 (2001).
Wu et al., "Adeno-Associated Virus Serotypes: Vector Toolkit or Human Gene Therapy," *Molecular Therapy*, pp. 316-327 (2006).
Waterkamp et al., "Isolation of Targeted AAV2 Vectors from Novel Virus Display Libraries," *The Journ. of Gene Medicine*, pp. 1307-1319 (2006).

(Continued)

*Primary Examiner* — Jean Witz
*Assistant Examiner* — Mindy Newman
(74) *Attorney, Agent, or Firm* — Foley & Lardner LLP (57) ABSTRACT

The present invention is concerned with the provision of a polynucleotide encoding an AAV capsid polypeptide comprising an inserted peptide and a vector comprising said polynucleotide. Moreover, contemplated is a host cell comprising said polynucleotide or vector, a method for the manufacture of said capsid polypeptide as well as said polypeptide. Further included is an antibody specifically binding to said polypeptide and a medicament comprising said polynucleotide, vector, polypeptide, or antibody. Also contemplated are the use of said polynucleotide, vector, polypeptide, or antibody for the manufacture of a medicament for the treatment of vascular disease and a method for the identification of a compound binding to said polypeptide.

16 Claims, 4 Drawing Sheets

OTHER PUBLICATIONS

Muller et al., "Random peptide libraries displayed on adeno-associated virus to select for targeted gene therapy vector," *Nature Biotechnology*, pp. 1040-1046 (2003).

Michelfelder et al., "Vectors selected from adeno-associated viral display peptide libraries for leukema cell-targeted cytotoxic gene therapy," *Experimental Hematology*, pp. 1766-1776 (2007).

Kwon et al., "Designer Gene Delivery Vectors: Molecular Engineering and Evolution of Adeno-Associated Viral Vectors for Enhanced Gene Transfer," *Pharmaceutical Research*, pp. 489-499 (2008).

Walensky et al., "Activation of Apoptosis in Vivo by a Hydrocarbon-Stapled BH3 Helix," *Science*, pp. 1466-1470 (2004).

Walensky Supplemental Material Experimental Procedures, "Synthesis of Stabilized Alpha-Helix of BCL-2 Domain (SAHB) Compounds" (2004) pp. 1-25.

Snyder et al., "Cell Penetrating Peptides in Drug Delivery," *Pharmaceutical Research*, pp. 389-393 (2004).

Genbank Acc. No. AAC55049, GI:1408469, Muramatsu et al., Capsid Protein, [Adeno-associated virus—3], (1996).

Genbank Acc. No. AAC58045.1, GI:2337940, Chiorini et a l, Capsid [Adeno-associated virus—4], (1997).

Genbank Acc. No. AAC03780.1, GI:2906023, Ruffing et al., Major Coat Protein VP1 [Adeno-associated virus—2], (1994).

Genbank Acc. No. AAD13756, GI:4249658, Chiorini et al., Capsid Protein, [Adeno-associated virus—5], (1999).

Genbank Acc. No. AAD27757, GI:4689097, Xiao et al., Capsid Protein, [Adeno-associated virus—1], (1999).

Genbank Acc. No. AAN03855.1, GI:22652861, Gao et al., Capsid Protein, [Adeno-associated virus—7], (2002).

Genbank Acc. No. AF513852_2, GI:22652864, Gao et al., Capsid Protein, [Adeno-associated virus—8], (2002).

Genbank Acc. No. AAS99264, GI:46487805, Gao et al., Capsid Protein VP1 [Adeno-associated virus—9], (2004).

Genbank Acc. No. AAT46337.1, GI:48728343, Mori et al., Capsid Protein, [Adeno-associated virus—10], (2004).

Genbank Acc. No. AAT46339.1, GI:48728346, Mori et al., Capsid Protein, [Adeno-associated virus—11], (2004).

Genbank Acc. No. AB116639.1, GI:112379656, Schmidt et al., VP1, [Adeno-associated virus—12], (2004).

Genbank Acc. No. ABZ10812.1, GI:167047087, Schmidt et al., Capsid Protein, [Adeno-associated virus—13], (2008).

SEQUENCE LISTING

```
<160> NUMBER OF SEQ ID NOS: 17

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

Arg Gly Asp Leu Arg Val Ser
1               5

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asn Asn Val Arg Gly Phe Val
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Ile Arg Ser Pro Pro Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Leu Arg Ser Pro Pro Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asn Phe Thr Arg Leu Ser Ala
1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Gly Asp Phe Arg Val Gly
1               5

<210> SEQ ID NO 7
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 7

Asn Leu His Ser Pro Pro Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide (pep 8)

<400> SEQUENCE: 8

Asn Asp Val Arg Ala Val Ser
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide (pep 9)

<400> SEQUENCE: 9

Thr Glu Trp Asp Gln Pro Phe
1               5

<210> SEQ ID NO 10
<211> LENGTH: 42
<212> TYPE: DNA
<213> ORGANISM: Artificial Sequence
<220> FEATURE:
<223> OTHER INFORMATION: Description of Artificial Sequence: Synthetic
      primer forward

<400> SEQUENCE: 10
caattacaga ttacgagtca gatatcgtgc caatggggcg ag                          42

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Synthetic
      primer reverse

<400> SEQUENCE: 11
ctcgccccat tggcacgata tctgactcgt aatctgtaat tg                          42

<210> SEQ ID NO 12
<211> LENGTH: 56
<212> TYPE: DNA
<213> ORGANISM: Artificial Sequence
<220> FEATURE:
<223> OTHER INFORMATION: Description of Artificial Sequence: Synthetic
      random oligonucleotide
<220> FEATURE:
<221> NAME/KEY: modified_base
<222> LOCATION: (18)..(19)
<223> OTHER INFORMATION: a, c, t, g, unknown or other
<220> FEATURE:
<221> NAME/KEY: modified_base
<222> LOCATION: (21)..(22)
<223> OTHER INFORMATION: a, c, t, g, unknown or other
<220> FEATURE:
<221> NAME/KEY: modified_base
```

```
<222> LOCATION: (24)..(25)
<223> OTHER INFORMATION: a, c, t, g, unknown or other
<220> FEATURE:
<221> NAME/KEY: modified_base
<222> LOCATION: (27)..(28)
<223> OTHER INFORMATION: a, c, t, g, unknown or other
<220> FEATURE:
<221> NAME/KEY: modified_base
<222> LOCATION: (30)..(31)
<223> OTHER INFORMATION: a, c, t, g, unknown or other
<220> FEATURE:
<221> NAME/KEY: modified_base
<222> LOCATION: (33)..(34)
<223> OTHER INFORMATION: a, c, t, g, unknown or other
<220> FEATURE:
<221> NAME/KEY: modified_base
<222> LOCATION: (36)..(37)
<223> OTHER INFORMATION: a, c, t, g, unknown or other

<400> SEQUENCE: 12
cagtcggcca agcaggcnnk nnknnknnkn nknnknnkgc ccaggcggct gacgag        56

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      second strand primer

<400> SEQUENCE: 13
ctcgtcagcc gcctgg                                                    16

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      rescue forward primer

<400> SEQUENCE: 14
ggaggatccg caggtacagg tgtgt                                          25

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      rescue reverse primer

<400> SEQUENCE: 15
gcttgatgaa ttctggacct gctatggc                                      28

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      sequencing primer

<400> SEQUENCE: 16
caaacaagga actggaagag                                                20

<210> SEQ ID NO 17
<211> LENGTH: 6
<212> TYPE: PRT
<213> ORGANISM: Artificial Sequence
```

-continued

```
<220> FEATURE:
<223> OTHER INFORMATION: Description of Artificial Sequence: Synthetic
      6xHis tag

<400> SEQUENCE: 17

His His His His His His
1               5
```

MODIFIED AAV CAPSID POLYPEPTIDES

SEQUENCE LISTING

The instant application contains a Sequence Listing which has been submitted in ASCII format via EFS-Web and is hereby incorporated by reference in its entirety. Said ASCII copy, created on Apr. 2, 2012, is named 97147120.txt and is 4,736 bytes in size.

The present invention is concerned with the provision of a polynucleotide encoding an AAV capsid polypeptide comprising an inserted peptide and a vector comprising said polynucleotide. Moreover, contemplated is a host cell comprising said polynucleotide or vector, a method for the manufacture of said capsid polypeptide as well as said polypeptide. Further included are an antibody specifically binding to said polypeptide and a medicament comprising said polynucleotide, vector, polypeptide, or antibody. Also contemplated are the use of said polynucleotide, vector, polypeptide, or antibody for the manufacture of a medicament for the treatment of vascular disease and a method for the identification of a compound binding to said polypeptide.

Gene therapy approaches have been investigated in cardiology mainly in two fields: First, in the treatment of ischemic heart disease and other acquired disorders it is sufficient to obtain a localized and transient expression of the therapeutic gene. Second, in inherited disease, a homogeneous gene transfer throughout the heart leading to sustained expression of the therapeutic gene is required. Adeno-Associated Virus (AAV) vectors have been known to enable transfer and long-term expression of therapeutic genes in the heart and skeletal muscle. The different serotypes of AAV have been shown to have different tropisms within the body, with AAV9 e.g. having the highest tropism for the murine heart. Transduction efficiencies obtainable with AAV vectors comprising unmodified capsids. However, they are far too low to be of therapeutic use.

Using AAV2 as a model system, the feasibility of using a random peptide display library to select for AAV2 vectors with improved efficiency and specificity of endothelial gene transfer has been shown. However, efficient in vivo gene transfer with AAV2 is hampered by the fact that most individuals comprise neutralizing antibodies against this type of virus. Furthermore, overall transduction efficiency with AAV2 vectors in animal models is low, so that there is also need in the art for a system allowing highly efficient gene transfer into endothelial cells in animal models.

Thus, the present invention relates to a polynucleotide encoding an AAV capsid polypeptide comprising an inserted peptide as shown in any one of SEQ ID Nos. 1 to 7.

In the expression "polynucleotide encoding an AAV capsid polypeptide" as used in accordance with the present invention, the term "Adeno-Associated Virus" or "AAV" relates to the group of viruses containing a short (approx. 4.7 kB) single-stranded DNA and depending in their lytic replication on the presence of an Adenovirus. AAVs are members of the Parvoviridae family of viruses. Also contemplated by the present invention are vectors derived from AAV, i.e. gene transfer vehicles using the capsid polypeptide of AAV to mediate the transfer of recombinant polynucleic acids into target cells. The term "capsid polypeptide" as meant herein relates to a polypeptide with the activity of self-assembly to produce the proteinaceous shell of an AAV particle, also referred to as coat protein or VP protein. It is to be understood that not all AAV capsid polypeptide molecules in a given cell assemble into AAV capsids. Preferably, at least 25%, at least 50%, at least 75%, at least 85%, at least 90%, at least 95% of all AAV capsid polypeptide molecules assemble into AAV capsids. Suitable assays for measuring this biological activity are described e.g. in Smith-Arica and Bartlett (2001), Curr Cardiol Rep 3(1): 43-49. Preferably, the capsid polypeptide is the capsid polypeptide of AAV1 (Genbank Acc. No: AAD27757.1, GI:4689097), AAV2 (Genbank Acc. No: AAC03780.1, GI:2906023), AAV3 (Genbank Acc. No: AAC55049.1, GI:1408469), AAV4 (Genbank Acc. No: AAC58045.1, GI:2337940), AAV5 (Genbank Acc. No: AAD13756.1, GI:4249658), AAV7 (Genbank Acc. No: AAN03855.1, GI:22652861), AAV8 (Genbank Acc. No: AAN03857.1, GI:22652864), AAV10 (Genbank Acc. No: AAT46337.1, GI:48728343), AAV11 (Genbank Acc. No: AAT46339.1, GI:48728346), AAV12 (Genbank Acc. No: ABI16639.1, GI:112379656), AAV13 (Genbank Acc. No: ABZ10812.1, GI:167047087), or, most preferably, AAV9 (Genbank Acc. No: AAS99264.1, GI:46487805).

"Polynucleotide" relates to a polynucleotide comprising a nucleic acid sequence which encodes a polypeptide having the biological activity as described above. It is to be understood that a polypeptide having an amino acid sequence as detailed above may also be encoded due to the degenerated genetic code by more than one species of polynucleotide.

Moreover, the term "polynucleotide" as used in accordance with the present invention further encompasses variants of the aforementioned specific polynucleotides. Said variants may represent orthologs, paralogs or other homologs of the polynucleotide of the present invention. The polynucleotide variants, preferably, comprise a nucleic acid sequence characterized in that the sequence can be derived from the aforementioned specific nucleic acid sequences by at least one nucleotide substitution, addition and/or deletion whereby the variant nucleic acid sequence shall still encode a polypeptide having the activity as specified above. Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N.Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If organic solvent is present in the abovementioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The abovementioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above.

Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptides of the present invention may be identified by a sequence comparison of the nucleic acid sequence of the polynucleotide or of the amino acid sequence of the polypeptides as specified above. Suitable PCR conditions are well known in the art. As a template, DNA or cDNA from AAVs may be used. Further, variants include polynucleotides comprising nucleic acid sequences which are at least 70%, at least 75%, at least 80%, at least 85%, at least 90%, at least 95%, at least 98% or at least 99% identical to the nucleic acid sequences detailed above. Moreover, also encompassed are polynucleotides which comprise nucleic acid sequences encoding amino acid sequences which are at least 70%, at least 75%, at least 80%, at least 85%, at least 90%, at least 95%, at least 98% or at least 99% identical to the amino acid sequences referred to above. The percent identity values are, preferably, calculated over the entire amino acid or nucleic acid sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (J. Mol. Evolution., 25, 351-360, 1987, Higgins et al., CABIOS, 5 1989: 151-153) or the programs Gap and BestFit (Needleman and Wunsch (J. Mol. Biol. 48; 443-453 (1970)) and Smith and Waterman (Adv. Appl. Math. 2; 482-489 (1981))], which are part of the GCG software packet (Genetics Computer Group, 575 Science Drive, Madison, Wis., USA 53711 (1991)), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

A polynucleotide comprising a fragment of any of the aforementioned nucleic acid sequences is also encompassed as a polynucleotide of the present invention. The fragment shall encode a polypeptide which still has the biological activity as specified above. Accordingly, the polypeptide may comprise or consist of the domains of the polypeptide of the present invention conferring the said biological activity. A fragment as meant herein, preferably, comprises at least 50, at least 100, at least 250 or at least 500 consecutive nucleotides of any one of the aforementioned nucleic acid sequences or encodes an amino acid sequence comprising at least 20, at least 30, at least 50, at least 80, at least 100 or at least 150 consecutive amino acids of any one of the aforementioned amino acid sequences.

The polynucleotides of the present invention either essentially consist of the aforementioned nucleic acid sequences or comprise the aforementioned nucleic acid sequences. Thus, they may contain further nucleic acid sequences as well. Specifically, the polynucleotides of the present invention may encode fusion proteins wherein one partner of the fusion protein is a polypeptide being encoded by a nucleic acid sequence recited above. Such fusion proteins may, preferably, comprise as additional part polypeptides for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags (SEQ ID NO: 17), MYC-tags and the like.

The polynucleotide of the present invention shall be provided, either as an isolated polynucleotide (i.e. isolated from its natural context) or in genetically modified form. The polynucleotide, preferably, is DNA including cDNA or RNA. The term encompasses single as well as double stranded polynucleotides. Moreover, comprised are also chemically modified polynucleotides including naturally occurring modified polynucleotides such as glycosylated or methylated polynucleotides or artificially modified ones such as biotinylated polynucleotides.

The term "inserted peptide" as used herein relates to a peptide having a sequence as shown in any one of SEQ ID Nos. 1 to 7 which has been introduced intramolecularly into an AAV capsid polypeptide detailed above. Preferably, said insertion is at a site exposed to the exterior of the AAV capsid in a manner that does not interfere with the activity of said polypeptide in capsid assembly, more preferably the site is the position after the amino acid corresponding to amino acid 588 in AAV2 and most preferably the insertion is between amino acids 591 and 592 of the AAV9 capsid polypeptide.

In another preferred embodiment, the present invention relates to a vector comprising the polynucleotide of any one of claims 1 to 3.

The term "vector", preferably, encompasses phage, plasmid, viral or retroviral vectors as well as artificial chromosomes, such as bacterial or yeast artificial chromosomes. More preferably, vector relates to a vector derived from an AAV. Moreover, the term also relates to targeting constructs which allow for random or site-directed integration of the targeting construct into genomic DNA. Such targeting constructs, preferably, comprise DNA of sufficient length for either homologous or heterologous recombination. The vector encompassing the polynucleotides of the present invention, preferably, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerens. Alternatively, a plasmid vector may be introduced by heat shock or electroporation techniques. Should the vector be a virus, it may be packaged in vitro using an appropriate packaging cell line prior to application to host cells. Viral vectors may be replication competent or replication defective. In the latter case, viral propagation generally will occur only in complementing host/cells.

More preferably, in the vector of the invention the polynucleotide is operatively linked to expression control sequences allowing expression in prokaryotic or eukaryotic cells or isolated fractions thereof. Expression of said polynucleotide comprises transcription of the polynucleotide, preferably into a translatable mRNA. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40- enhancer or a globin intron in mammalian and other animal cells. Moreover, inducible expression control sequences may be used in an expression vector encompassed by the present invention. Such inducible vectors may, preferably, comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (InVitrogene) or pSPORT1 (GIBCO BRL). Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

The present invention also relates to a host cell comprising the polynucleotide of any one of claims 1 to 3 or the vector of claim 4.

As used in this specification, "host cell" preferably relates to a cell maintained in vitro in a suitable cultivation medium and capable of producing AAV capsid polypeptides.

Preferably, said host cell is a bacterial cell, a yeast cell, or an insect cell, and most preferably said host cell is a mammalian cell.

In a further preferred embodiment, the present invention relates to a method for the manufacture of a polypeptide comprising the steps of a) culturing a host cell comprising the polynucleotide of any one of claims 1 to 3 or the vector of claim 4 and b) obtaining the polypeptide encoded by said polynucleotide or vector from the host cell.

The method of the present invention, preferably, may comprise steps in addition to those explicitly mentioned above. For example, further steps may relate to providing a suitable number of cells to be used as host cells or separating capsids or capsid polypeptides from other proteins in the reaction mixture.

The term "culturing a host cell" as used herein relates to incubating a host cell comprising the properties as specified above under conditions suitable for the production of AAV capsid polypeptides. Preferably, said conditions are the conditions suited optimally for the growth of the respective host cell, which vary with the type of host cell and which are well known in the art (see, for example, Example 1).

The term "obtaining AAV capsid polypeptides" as used herein, preferably, relates to separating AAV capsid polypeptides from host cells in a way that makes AAV capsid polypeptides amenable for further use. Methods used for obtaining AAV capsid polypeptides are well known in the art. The choice of methods depends on the purity required and the further use intended. For example, AAV capsid polypeptides may be obtained by obtaining capsids comprising said polypeptides by centrifugation or by equilibrium centrifugation in CsCl density gradients. Other methods for obtaining AAV capsid polypeptides include but are not limited to affinity chromatography, heparin affinity chromatography, ion exchange chromatography, hydrophobic interaction chromatography, hydroxyapatite chromatography, or size exclusion chromatography, alone or in combination.

The term "polypeptide" as used herein refers to amino acid chains of between 50 to 1000 amino acids in length comprising the amino acid sequences encoded by the polynucleotides specified above. The polypeptide of the present invention can be recombinantly manufactured or may be chemically synthesised. The polypeptide may comprise further amino acids which may serve as a tag for purification or detection. Moreover, the polypeptide of the present invention may be comprised by a fusion polypolypeptide. The variant or modified polypeptides, preferably, retain the biological activity of forming AAV capsid structures. The conservation of activity can be tested by the one skilled in the art according to methods specified above.

The term "polypeptide" also includes chemically modified polypeptides, e.g., polypeptides containing modified amino acids or polypeptides which are, e.g., biotinylated, or are coupled to fluorophores, such as fluorescein, or Cy 3, are conformationally restricted, e.g. by disulfide bridging or by stapling (Walensky 2004, Science 305(5689): 1466-1470), or are linked to cell penetration polypeptides or protein transduction domains (Snyder 2004, Pharm Res 21(3): 389-393). Such modifications may improve the biological properties of the polypeptides, e.g., cell penetration, binding, stability, or may be used as detection labels.

In another preferred embodiment, the present invention relates to a polypeptide encoded by the polynucleotide of any one of claims 1 to 3 or which is obtainable by the method of claim 6.

Furthermore, the present invention also comprises an antibody which specifically binds to the polypeptide of claim 7.

Antibodies binding specifically to the polypeptides as specified above can be prepared by well known methods using a purified polypeptide according to the invention or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be synthetic peptides. Preferably, the antibody of the present invention is a monoclonal antibody, a polyclonal antibody, a single chain antibody, a human or humanized antibody or primatized, chimerized or fragment thereof. Also comprised as antibodies by the present invention are a bispecific antibody, a synthetic antibody, an antibody fragment, such as Fab, Fv or scFv fragments etc., or a chemically modified derivative of any of these. The antibody of the present invention binds specifically (i.e. does not cross react with other polypeptides or peptides) to the polypeptide of the invention. Specific binding can be tested by various well known techniques.

Antibodies or fragments thereof can be obtained by using methods which are known to the person skilled in the art. Monoclonal antibodies can be prepared by a fusion of mouse myeloma cells to spleen cells derived from immunized mammals, a technique which can be used by the skilled artisan without further ado.

The antibodies are used, for example, for the immunoprecipitation and immunolocalization of the polypeptides of the invention as well as for the monitoring of the presence of said polypeptides, preferably, in recombinant organisms, and for the identification of compounds interacting with the polypeptides according to the invention. More preferably, the antibodies of the present invention are used to neutralize AAV particles comprising capsid polypeptides of the present invention. Thus the antibodies of the present invention are, preferably, also of therapeutic use.

In a further preferred embodiment, the present invention relates to a medicament comprising the polynucleotide of any one of claims 1 to 3, the vector of claim 4, the polypeptide of claim 7, or the antibody of claim 8.

The term "medicament" as used herein comprises the compounds of the present invention and optionally one or more pharmaceutically acceptable carrier. The compounds of the present invention can be formulated as pharmaceutically acceptable salts. Acceptable salts comprise acetate, methylester, HCl, sulfate, chloride and the like. The medicaments are, preferably, administered topically or systemically. Suitable routes of administration conventionally used for drug administration are oral, intravenous, or parenteral administration as well as inhalation. However, depending on the nature and mode of action of a compound, the medicaments may be administered by other routes as well. For example, polynucleotide compounds may be administered in a gene therapy approach by using viral vectors or viruses or liposomes.

Moreover, the compounds can be administered in combination with other drugs either in a common medicament or as separated medicaments wherein said separated medicaments may be provided in form of a kit of parts.

The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

The carrier(s) must be acceptable in the sense of being compatible with the other ingredients of the formulation and being not deleterious to the recipient thereof. The pharmaceutical carrier employed may be, for example, either a solid, a gel or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the combination. Examples of such diluents are distilled water, physiological saline, Ringer's solutions, dextrose solution, and Hank's solution. In addition, the medicament or formulation may also include other carriers, adjuvants, or nontoxic, nontherapeutic, nonimmunogenic stabilizers and the like.

Specific medicaments are prepared in a manner well known in the pharmaceutical art and comprise at least one active compound referred to herein above in admixture or otherwise associated with a pharmaceutically acceptable carrier or diluent. For making those specific medicaments, the active compound(s) will usually be mixed with a carrier or the diluent, or enclosed or encapsulated in a capsule, sachet, cachet, paper or other suitable containers or vehicles. The resulting formulations are to be adopted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

A therapeutically effective dose refers to an amount of the compounds to be used in a medicament of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors, preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 µg; however, doses below or above this exemplary range are envisioned, especially considering the aforementioned factors. Generally, the regimen as a regular administration of the medicament should be in the range of 1 µg to 10 mg units per day. If the regimen is a continuous infusion, it should also be in the range of 1 µg to 10 mg units per kilogram of body weight per minute, respectively. In studies employing viral vectors, however, vector doses usually are indicated by "genome copies (gc)" or "vector genomes (vg)". Doses ranging between $10^{12}$ to $10^{14}$ are thereby realistic for large animal or human trials. Progress can be monitored by periodic assessment.

The medicaments and formulations referred to herein are administered at least once in order to treat or ameliorate or prevent a disease or condition recited in this specification. However, the said medicaments may be administered more than one time, for example from one to four times daily up to a non-limited number of days.

Further encompassed by the present invention is a polynucleotide, the vector, the polypeptide or the antibody of the present invention for use as a medicament for the treatment or prevention of a vascular disease. It will be understood that the present invention in this context also provides for a method for the manufacture of a medicament for the treatment or prevention of a vascular disease comprising formulating the polynucleotide, the vector, the polypeptide or the antibody of the present invention in a pharmaceutically acceptable form.

The term "vascular disease" as used herein refers to an acquired or inherited disease of the vascular system. The term "acquired vascular disease", preferably, includes, but is not limited to, aortic aneurysm, aortic dissection, Buerger's disease, carotid artery disease, critical limb ischemia, chronical venous insufficiency, deep vein thrombosis, lymphedema, peripheral arterial disease, portal hypertension, Raynaud's disease, renovascular hypertension, stroke, acquired thrombophilia, varicose veins, cardiac allo graft vasculopathy, venous or arterial bypass stenosis, and myocardial infarction. The term "inherited vascular disease" relates to an inherited disease showing at least one symptom in the vascular system. Inherited diseases having vascular symptoms include, but are not limited to, Marfan syndrome, congenital vascular malformation, and inherited thrombophilia.

The term "treatment" refers to the amelioration of the diseases or disorders referred to herein or the symptoms accompanied therewith to a significant extent. Treatment as used herein also includes an entire restoration of the health with respect to the diseases or disorders referred to herein. It is to be understood that treatment as used in accordance with the present invention may not be effective in all subjects to be treated. However, the term shall require that a statistically significant portion of subjects suffering from a disease or disorder referred to herein can be successfully treated. Whether a portion is statistically significant can be determined without further ado by the person skilled in the art using various well known statistic evaluation tools, e.g., determination of confidence intervals, p-value determination, Student's t-test, Mann-Whitney test etc. Preferred confidence intervals are at least 90%, at least 95%, at least 97%, at least 98% or at least 99%. The p-values are, preferably, 0.1, 0.05, 0.01, 0.005, or 0.0001. Preferably, the treatment shall be effective for at least 60%, at least 70%, at least 80%, or at least 90% of the subjects of a given cohort or population.

The term "prevention" refers to retaining health with respect to the diseases or disorders referred to herein for a certain period of time in a subject. It will be understood that the said period of time is dependent on the amount of the drug compound which has been administered and individual factors of the subject discussed elsewhere in this specification. It is to be understood that prevention may not be effective in all subjects treated with the compound according to the present invention. However, the term requires that a statistically significant portion of subjects of a cohort or population are effectively prevented from suffering from a disease or disorder referred to herein or its accompanying symptoms. Preferably, a cohort or population of subjects is envisaged in this context which normally, i.e. without preventive measures according to the present invention, would develop a disease or disorder as referred to herein. Whether a portion is statistically significant can be determined without further ado by the person skilled in the art using various well known statistic evaluation tools discussed above.

In a still further preferred embodiment, the present invention relates to a method for the identification of a compound binding to the polypeptide of claim 6 or 7 comprising the steps of a) contacting said polypeptide with a target cell and b) identifying compounds bound to said polypeptide.

The term "target cells" as used herein relates to cells binding to an AAV capsid polypeptide of this invention maintained in vitro in a suitable cultivation medium. Preferably, said cells are mammalian cells and most preferably they are human cells.

The term "compound binding to the polypeptide", preferably, refers to a molecule, more preferably a peptide or polypeptide. Said compound shall be capable of binding to the AAV capsid polypeptide of this invention. Suitable compounds may be obtained by fractioning extracts from biological organisms, preferably from target cells. Suitable compounds can also be generated by in silico screening methods based on, e.g., molecular modelling approaches.

The term "contacting" as used herein may be carried out by mixing the components referred to in step a) in vitro. Suitable conditions can be adjusted by the skilled artisan without further ado.

Methods to determine the amount of a compound bound to a polypeptide are well known in the art and include, but are not limited to, e.g., equilibrium dialysis, south-western blotting or plasmon surface resonance measurement. Preferably, said interaction leads to an accumulation of said compound in the vicinity of said polypeptide. Preferably, accumulation of said compound can be detected by visible or microscopical inspection either as a result of the physical properties of said compound or after chemical modification of said compound, e.g. conjugation to a colored or color-producing compound.

All references referred to above are herewith incorporated by reference with respect to their entire disclosure content as well as their specific disclosure content explicitly referred to in the above description.

FIGURES

FIG. 1: FACS analysis of transduction efficiencies of wt and mutant scAAV9 (scAAV2) vectors. Wt AAV2 and wt scAAV9 GFP-vectors were compared to mutant vectors expressing the peptide motif NDVRAVS (SEQ ID NO: 8) at amino acid site 588 (AAV2) or 591 (AAV9). Two independent vector productions of each construct were repeat-determined at a MOI of $10^4$ genome copies (gc)/cell (HCAEC) and 72 h later percentage of GFP-positive cells was monitored by FACS. The so obtained data set of 4 individual values per construct ("single data"), was averaged ("mean values", columns) and standard deviation was calculated (error bars).

FIG. 2: Titer studies of wt and mutant AAV9 virus productions. Wild-type AAV9 viruses (wt AAV9) and mutants harboring heptapeptide motif NDVRAVS (SEQ ID NO: 8) at position 591 (AAV9-NDVRAVS ("NDVRAVS" disclosed as SEQ ID NO: 8)) were produced and were analysed by quantitative real-time PCR (genomic titer, gc/ml) and infectious center assays on HeLa cells (infectious titer, iu/ml). For control, a virus production involving empty pKV-AAV9Lib/BB (AAV9-no insert) was included. Statistical analysis was not performed due to single measurements.

FIG. 3: Transduction efficiencies of wt and mutant AAV9 vectors on HCAEC. Wt and two control mutants, NDVRAVS (SEQ ID NO: 8) (positive) and TEWDQPF (SEQ ID NO: 9) (negative) together with seven mutants expressing enriched peptide motives of an AAV9 random heptapeptide library selected over 4 rounds on HCAEC were used to construct GFP-vectors. Two independent vector productions of each construct were incubated with HCAEC at MOIs of 1000 gc/cell for 24 or 48 h, respectively. Transduction efficacies were repeat-determined by FACS. FIG. 3 discloses SEQ ID NOS 8, 9, 1, 6, 5, 7, and 2-4, respectively, in order of appearance.

FIG. 3a discloses SEQ ID NOS 8, 9, 1, 6, 5, 7, and 2-4, respectively, in order of appearance.

The invention will now be illustrated by the following Examples which are not intended to restrict or limit the scope of this invention.

EXAMPLES

Example 1

Cell Culture and Virus Production

Human coronary artery endothelial cells (HCAEC) were maintained in the medium supplied by the cell provider (Promocell), additionally, 1% Penicillin/Streptomycin was subjoined. 293T or HeLa cells were maintained in Dulbecco's modified Eagle medium (DMEM) with 10% FBS, 2 mM L-Glutamine and 1% Penicillin/Streptomycin. Transfections were performed by polyethylenimine (PET, N/P=20).

For production of self-complementary AAV9 (scAAV9) GFP-vectors, 293T cells were transfected with the p5E18-VD2/9 plasmid for generation of wild-type capsids or with the p5E18-VD-2/9-SfiI1759 for generation of mutant capsids, along with pDGΔVP containing the adenovirus helper functions and the EGFP-expressing, ITR-positive plasmid pdsAAV-CMV-EGFP. After harvesting, vectors were purified by using iodixanol gradients and titered by quantitative real-time PCR (TaqMan, Applied Biosystems) using CMV-specific primers and probe.

Production of AAV9 viruses occurred by using ITR-positive plasmid pKV-wtAAV9 for generation of wild-type capsids and pKV-AAV9Lib/BB with an inserted oligonucleotide for generation of mutant capsids along with pDGΔVP.

For production of AAV9 library virus, "transfer shuttle libraries" (TSL) were first generated by transfecting 293T cells with the ITR-positive pKV-AAV9Lib plasmids along with pDGΔVP and ITR-negative pRSV-VP3co, a plasmid expressing the codon-optimized wild-type (wt) AAV2 VP3-capsid protein. After harvesting the transfer shuttle library, particles were purified by using iodixanol gradients. Titering of infectious units occurred by an infectious center assay (ICA) using a radioactively labeled rep2-specific probe and 293T (TSL) or HeLa cells (AAV9 viruses). 293T cells were infected then with the TSL and wt Ad5 was used for library particle amplification. ICA and infection of 293T with TSL was carried out in DMEM with 5% FBS, 2 mM L-Glutamine and 1% Penicillin/Streptomycin. After harvesting, AAV9 virus library particles were purified by using iodixanol gradients and titered by quantitative real-time PCR using rep2-specific primers and probe.

Example 2

AAV9 Library Backbone and Wild-Type AAV9 Plasmid

The plasmid pKV-AAV9Lib/BB serving as a backbone for cloning of the random oligonucleotides was developed from p5E18-VD-2/9, which contains the wt-sequences rep from AAV2 and cap from AAV9 (rep2/cap9 wt) but lacks ITRs. A 975 bp fragment of the wt AAV9 cap open reading frame was synthetically generated (Geneart, plasmid pGA4) harboring within cap9 at nucleotide position 1759 two incompatible SfiI restriction sites separated by a 2 bp stuffer fragment. Both plasmids were digested with BsiWI and XcmI and the mutated 975 bp cap9 fragment (cap9mut) from pGA4 was ligated into the empty p5E18-VD-219 backbone. The new plasmid was labeled p5E18-VD-2/9-SfiI1759 and served both for production of mutant vectors and as a cap9mut-donor for the creation of the ITR-positive library plasmid.

To create the library plasmid, first, p5E18-VD-2/9-SfiI1759 was digested with HindIII and EcoRV and the released 2774 bp fragment containing entire cap9mut was cloned into HindIII/EcoRV-digested pMT-187-XX2 backbone, an ITR-negative plasmid harboring the wt AAV2 rep and cap sequences (rep2/cap2). To enable the HindIII/EcoRV-digestion of pMT-187-XX2, the EcoRV-site was generated by in vitro-mutagenesis (Stratagene) using forward 5'-CAA TTA CAG ATT ACG AGT CAG ATA TCG TGC CAA TGG GGC GAG-3' (SEQ ID No. 10) and reverse 5'-CTC GCC CCA TTG GCA CGA TAT CTG ACT CGT AAT CTG TAA TTG-3' (SEQ ID No. 11) primers. The resulting plasmid was named pMT-187-XX2-rep2/cap9mut. Then, ITR-positive plasmid pBS-SSV9 containing also rep2/cap2 and pMT-187-XX2-rep2/cap9mut were digested with XbaI, releasing rep2/cap2 and rep2/cap9mut, respectively. The latter was ligated into pBS-SSV9 backbone resulting into the ITR-positive rep2/cap9mut plasmid pKV-AAV9Lib/BB. Plasmid pKV-wtAAV9 was also created which was used for the production of wt AAV9 viruses. For that, plasmid p5E18-VD-2/9 was digested with HindIII and EcoRV and the 2764 bp fragment containing the entire cap9 wt fragment was cloned into HindIII/EcoRV-digested pMT-187-XX2 backbone resulting in plasmid pMT-187-XX2-rep2/cap9 wt. ITR-positive plasmid pBS-SSV9 and pMT-187-XX2-rep2/cap9 wt were digested with XbaI, releasing rep2/cap2 and rep2/cap9 wt, respectively. The latter was ligated into pBS-SSV9 backbone resulting into the ITR-positive rep2/cap9 wt plasmid pKV-wtAAV9.

Example 3

Generation of Random Libraries

The oligonucleotide insert was designed to display two different BglI restriction sites on each end allowing for directional in-frame cloning into the SfiI digested pKV-AAV9Lib/BB plasmid. The following degenerate oligonucleotide encoding a random seven-residue peptide insert at nucleotide position 1771 in the AAV9 cap gene was synthesized (University of Freiburg Oligonucleotide Synthesis Core Facility): 5'-CAG TCG GCC AAG CAG GC (NNK)7 GCC CAG GCG GCT GAC GAG-3' (SEQ ID No. 12). Second strand synthesis was done by using the sequenase enzyme from the Sequenase Kit (Amersham) and the second strand primer 5'-CTC GTC AGC CGC CTG G-3' (SEQ ID No. 13). The double-stranded insert was purified using the QIAquick Nucleotide Removal Kit (Qiagen). The 12 bp stuffer within pKV-AAV9Lib/BB was cleaved by SfiI-digestion and the plasmid was purified using the QIAquick PCR Purification Kit (Qiagen). Plasmid backbone and insert were ligated in a 1:30 molar ratio. Ligated plasmids were transformed into electrocompetent DH5α bacteria using the Gene Pulser (Biorad). Plasmid library diversity was determined by the number of clones growing from a representative aliquot of the transformed bacteria on agar plates containing 100 μg/ml ampicillin. Transformed bacteria were grown o/n at 30° C. to an OD600 of 0.2 and the library plasmids termed pKV-AAV9Lib were purified using Qiagen's Plasmid Prep Kit. 79 randomly picked clones from the plasmid library were sequenced to verify the presence of the random insert.

The AAV display peptide library was made from plasmids in a two-step system. First, the AAV library genomes were packaged into chimerical wild-type and mutant AAV capsids (TSL). For this, $10^8$ 293T cells were co-transfected using a 1:1:15 ratio of the pRSV-VP3co plasmid, the library plasmid pKV-AAV9Lib and the pDGΔVP helper plasmid (each plasmid at a total amount of 20, 20 or 300 μg, respectively). The resulting AAV library transfer shuttles were harvested after 72 h, purified (resulting in a total volume of 2 ml) and titered.

The random AAV display peptide library was obtained by infection of 293T cells with the AAV library transfer shuttles at an MOI of 1 replicative unit per cell and superinfection with Ad5 at a MOI of 5 infectious particles (ip)/cell. Cells were harvested 48 h later and virus was purified, resulting in a final volume of 2 ml.

$5 \times 10^7$ 293T cells were co-transfected using a 1:15 ratio of pKV-wtAAV9 (for wt viruses), pKV-AAV9Lib/BB with peptide motif NDVRAVS (SEQ ID NO: 8) (for mutant viruses) or empty pKV-AAV9Lib/BB plasmid (control) along with pDGΔVP (each plasmid at a total amount of 20 or 300 µg, respectively). The resulting AAV viruses were harvested after 72 h, purified (resulting in a total volume of 2 ml) and titered.

Example 4

AAV9 Random Peptide Screening $1.1 \times 10^6$ primary HCAEC were infected with an AAV9 display peptide library at a MOI of 10, 100 or 1000 gc/cell. After 4 h cells were washed with PBS followed by incubation with Ad5 in fresh medium at a MOI of 20 ip/cell until a cytopathic effect was observed. Replicated AAV particles were harvested from cell lysates and titered. For each of the 3 subsequent selection rounds on HCAEC, preselected AAV library particles were reapplied to the target cells at the MOIs mentioned above.

DNA extracted from cell lysate and AAV by the QIAamp Tissue Kit (Qiagen) served as a template for a PCR with the primers 5'-GGA GGA TCC GCA GGT ACA GGT GTG T-3' (SEQ ID No. 14) and 5'-GCT TGA TGA ATT CTG GAC CTG CTA TGG C-3' (SEQ ID No. 15). Resulting PCR products of 467 bp length were analyzed by gel electrophoresis, cloned into the pCR4®-TOPO® by TA-cloning® (Invitrogen) and randomly assigned clones were sequenced using the primer 5'-CAA ACA AGG AAC TGG AAG AG-3' (SEQ ID No. 16).

To obtain mutant scAAV9 GFP-vectors, first, oligonucleotides encoding the desired peptide motif were designed to be flanked by a sequence compatible to SfiI. Prior to ligation into p5E18-VD-2/9-SfiI1759, the plasmid was digested with SfiI and the 12 bp stuffer fragment was separated from the backbone by using the QIAquick PCR Purification Kit (Qiagen). Then, $10^8$ 293T cells were co-transfected with pds-AAV-CMV-EGFP harboring an enhanced GFP gene, the modified p5E18-VD-2/9-SfiI1759, and pDGΔVP at a ratio of 1:1.2:3.5 (each plasmid at a total amount of 200, 240 or 700 µg, respectively). Vector particles were harvested after 72 h, purified (resulting in a total volume of 2 ml) and titered. We seeded $5 \times 10^4$ HCAEC/well in 12-well plates and incubated them 24 h later with scAAV9 EGFP-vectors in 5000 medium at a MOI of $10^3$ and $10^4$ gc/cell. After 24 h and 48 h, respectively, cells were harvested and reporter gene activity was determined by FACS-assay (FACS Calibur, BD).

Example 5

Amino Acid Site 591 Plays a Role in the Infection Process of AAV9 Vectors

Mapping of antigenic and heparin binding regions as well as structural analyses of AAV serotype 2 have revealed several sites within the AAV capsid amenable to incorporation of targeting peptides. Inserting suitable peptides into loop IV of VP1-3 retargets AAV2 vectors to cells poorly susceptible to wt AAV2 forming the basis for the rational design of new ligand insertion sites. Building on these studies, random peptide libraries displayed on the surface of AAV2 were designed. The library peptides were positioned such that they were exposed on the surface of the vector capsid at a site (R588) critical for viral attachment to the target cell, thereby diminishing the vector's nonspecific endogenous tropism.

This critical site for viral attachment to its host cell has not been revealed yet for AAV9. However, DNA alignment studies of the cap genes of wt AAV2 and wt AAV9 have shown partially conserved sequences flanking R588. Therefore, it was reasoned that the same site could play a relevant role in the infection process of AAV9. Due to an additional amino acid present in the AAV9 cap gene and to a deletion of 2 amino acids in the modified cap gene of AAV2 employed in library creation, the analogous amino acid position to R588 is Q591. Due to differences in the capsid amino acid composition, the analogous amino acid position to R588 (wt AAV2) is A589 (wt AAV9). The design of the insertion site places the first amino acid of the inserted peptide motifs at position 590 (AAV2-library) and 591 (AAV9-library). In the wild-type capsid of AAV9, position 591 is occupied by an Alanine.

To test this hypothesis, wt and mutant AAV9 GFP-vectors were generated. Mutant vectors expressed the peptide motif NDVRAVS (SEQ ID NO: 8) at amino acid position 591. This motif was identified after selection of an AAV2 random heptapeptide library on HCAEC and was shown to enhance transduction efficacy of AAV2 vectors on HCAEC.

Figure 1:
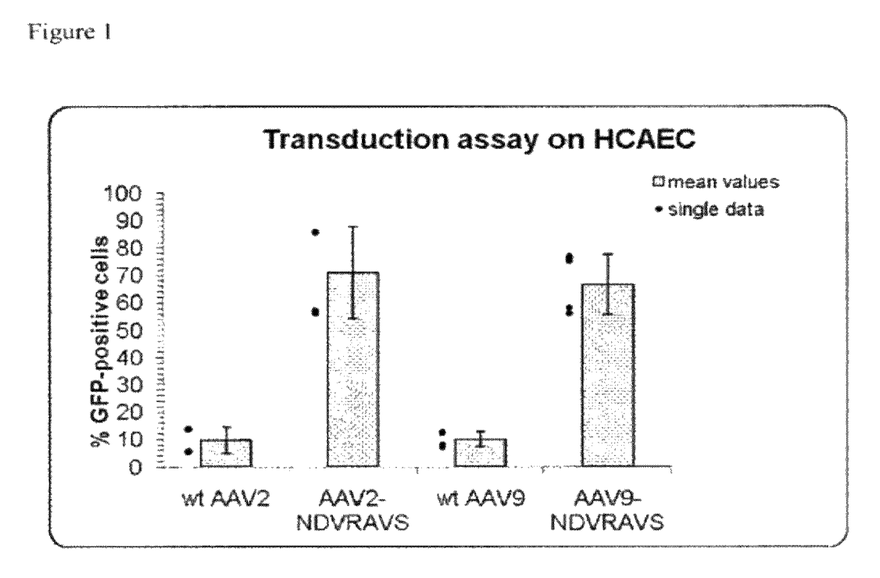

Mutant AAV9 vector titers similar to those of wt AAV9 proved, that insertion of heptapeptide motives at position 591 is tolerable during capsid assembly (data not shown). As a control, we also generated wt and mutant (NDVRAVS (SEQ ID NO: 8), amino acid position 588) AAV2 vectors. HCAEC were infected with a MOI of $10^4$ gc/cell for each vector and were incubated for 72 h. Furthermore, to compensate differences in infectivity in different productions of a construct, two independent vector productions for each vector were analyzed. Evaluation of GFP-fluorescence by FACS revealed that the AAV9 (AAV2) mutant bearing NDVRAVS (SEQ ID NO: 8) at position 591 (588) significantly (p<0.01 for both) enhanced transduction efficiency to 66.8±13.6% (71.2±20.5%) when compared to wt vectors (FIG. 1). This result confirmed the assumption that amino acid site 591 plays an infection-relevant role for AAV9 vectors.

Example 6

Figure 2:
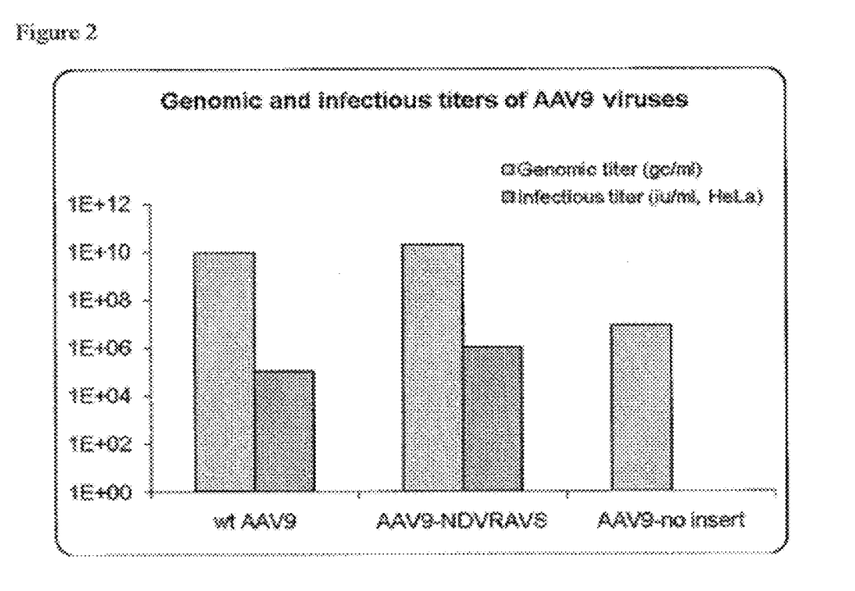

Insertion of Peptide Motives at Position 591 is Consistent with AAV9 Virus Infectivity The data obtained so far suggests that peptide insertions at capsid site 591 influences the transduction efficiency of AAV9 vectors. Yet unclear remains, whether a peptide insertion in the context of an AAV9 virus capsid retains the infectivity of wt AAV9. Therefore, it was investigated whether the insertion of peptide motif NDVRAVS (SEQ ID NO: 8) at capsid position 591 of AAV9 viruses—an inevitable step during the creation of an AAV9 virus library—would compromise the replication competence. Wt and mutant AAV9 viruses were produced and genomic as well as infectious titers were determined. Genomic titers for wt and mutant AAV9 viruses with NDVRAVS (SEQ ID NO: 8) insert were $8.7 \times 10^9$ and $1.9 \times 10^{10}$ gc/ml, respectively ($8.0 \times 10^6$ gc/ml without insert), and ICA detected $10^5$ (wt) versus $10^6$ (NDVRAVS (SEQ ID NO: 8)) infectious units/ml (FIG. 2). As expected, the control production involving empty pKV-AAV9Lib/BB did not yield infectious particles (FIG. 2, lane 3), as the stuffer fragment separating the SfiI-sites is designed to induce a frame shift within the cap9 open reading frame, thus compromising capsid assembly. Together, the comparable titer levels prove that a heptapeptide insertion at site 591 neither affects viral capsid assembly nor compromises the infectivity of AAV9 viruses.

Example 7

Generation, Evaluation, and Biopanning of AAV9 Random Peptide Library

The diversity of produced library plasmids was $6.2 \times 10^8$ clones per library. DNA sequencing of 79 clones verified that different random peptides were encoded in each clone. The representativeness of the 20 amino acids residues within the heptapeptide motif was consistent with statistically calculated distributions (data sets not shown). Based on the plasmid library, a transfer shuttle library was created and titering revealed a genomic titer of $1.0 \times 10^{12}$ gc/ml and an infectious titer of $5 \times 10^7$ iu/ml. The entire TSL was employed in the generation of the final AAV9 virus library and genomic titering yielded $2.6 \times 10^{11}$ gc/ml. DNA sequencing of 70 virus library clones verified the existence of different random peptides encoded in each clone and a statistical distribution of amino acid residues comparable to that of the plasmid library.

Using the virus library, a total of four consecutive selection rounds were performed on HCAEC and each round three different MOIs (10, 100, and 1000 gc/cell) were applied. After the 3rd and 4th selection round, aliquots from lysed cells were used for DNA purification and were subjected to PCR amplification and sequencing. Independent of selection round or employed MOI, peptide motif RGDLRVS (SEQ ID No 1) was the most abundant one.

Example 8

Enriched Peptide Motifs Confer to AAV9 Vectors Transduction Efficiencies Superior to Wt AAV9

To examine the transduction efficiency the enriched peptide motives confer to AAV9, seven of the most abundant peptide motives after 4 selection rounds were chosen: RGDLRVS (SEQ ID No. 1), NNVRGFV (SEQ ID No. 2), SIRSPPS (SEQ ID No. 3), SLRSPPS (SEQ ID No. 4), NFTRLSA (SEQ ID No. 5), RGDFRVG (SEQ ID No. 6) and NLHSPPA (SEQ ID No. 7). Oligonucleotides encoding the chosen peptides were ligated into plasmid p5E18-VD-2/9-SfiI1759 and GFP-expressing vectors were generated. Infected HCAEC with a MOI of $10^3$ or $10^4$ gc/cell for each vector were generated and each construct was incubated for 24 and 48 h, respectively. Furthermore, to compensate differences in infectivity in different productions of a construct, two independent vector productions for each vector were analyzed. In addition to the 7 aforementioned motives, wt and two mutant AAV9 vectors were used as controls. One of the mutants expressed NDVRAVS (SEQ ID No. 8) and served as a positive control and the other a non-selected randomly chosen motif TEWDQPF (SEQ ID No. 9) as a negative control.

Figure 3:
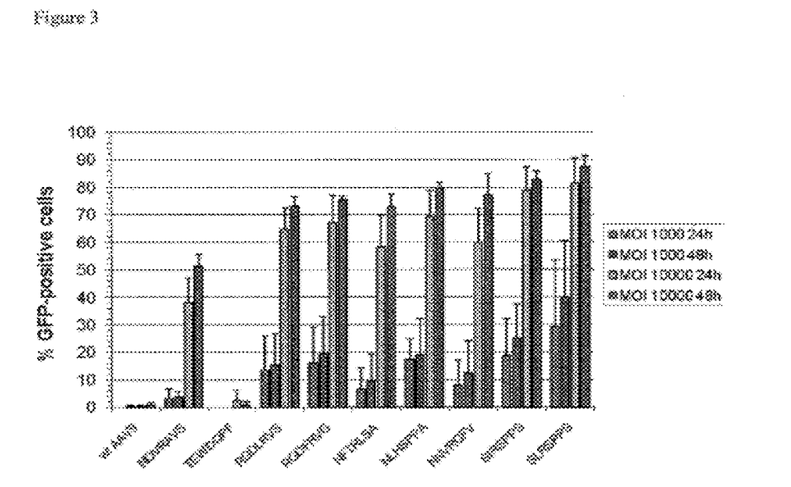
Figure 3A:
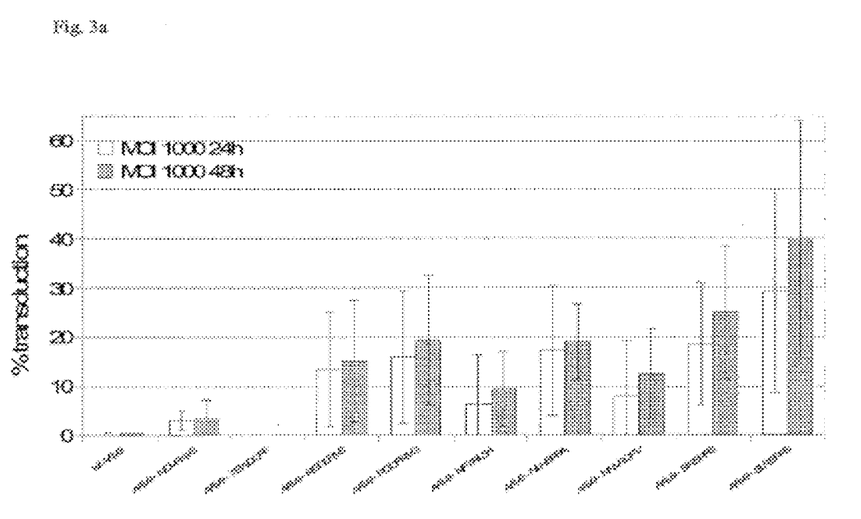
FIG. 3a: same as FIG. 3 except that representation is in greytone and that values for MOI=10000 were omitted for clarity.
Figure 4:
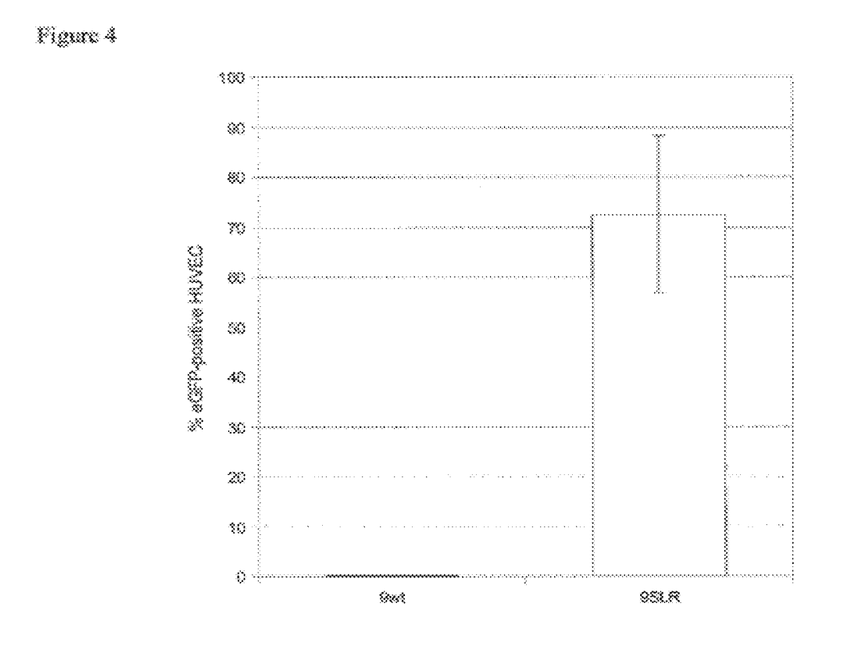
FIG. 4. Transduction efficiencies of endothelial cells in human umbilical veins in situ using self-complementary (sc) AAV9 CMV-eGFP vectors. Human umbilical veins from postnatally obtained umbilical cords were incubated for 2 h in situ with either wtAAV9 (9 wt) or AAV9-SLRSPPS ("SLRSPPS" disclosed as SEQ ID NO: 4) (9SLR) at a dose of 1.74E+9 gc/ml in HUVEC cell culture medium (Promocell, Heidelberg, Germany). Veins were flushed with PBS and HUVECs were isolated and cultivated in vitro for further 96 h. Percentage of eGFP-positive HUVECs from samples treated with either vector with AAV9 wild-type capsids or AAV9-SLRSPPS ("SLRSPPS" disclosed as SEQ ID NO: 4) capsids was determined by FACS-analysis (in relation to untreated cells). Averages are represented by blue bars (n=3), standard deviation by error bars.

Independent of MOI or incubation time, wt AAV9 vectors showed only basal transduction efficiency (FIG. 3). This was expected, as HCAEC is only very low permissive to this serotype. The positive control vector with NDVRAVS (SEQ ID No. 8)-insert reached a transduction efficiency of 3.53%±2.03% GFP-positive cells after the maximal incubation time of 48 h. Similar to the wt, mutant TEWDQPF (SEQ ID No. 9) confers no enhancement of transduction towards AAV9. This proves that the selection process of the AAV library is directed and enhancement of transduction occurs not by insertion of peptide motifs per se but is modulated by the amino acid sequence of the insertions. Vector mutant bearing peptide motif SLRSPPS (SEQ ID No. 4) confers after 24 h and 48 h of incubation at MOI of $10^3$ gc/cell a significantly enhanced transduction efficiency when compared to mutant NDVRAVS (SEQ ID No. 8) ($p<0.01$).

Example 9

An Enriched Peptide Motif Allows AAV9 Vectors to Transducer Quiescent Endothelial Cells in Human Umbilical Veins In Situ with High Efficiency To elucidate whether the selected motifs allow also an efficient transduction of a human vessel in situ, human umbilical veins were transduced with AAV9 CMV-eGFP vectors. Human umbilical veins from postnatally obtained umbilical cords were incubated for 2 h in situ with either wtAAV9 or AAV9-SLRSPPS ("SLRSPPS" disclosed as SEQ ID NO: 4) at a dose of 1.74E+9 gc/ml in HUVEC cell culture medium (Promocell, Heidelberg, Germany). Veins were flushed with PBS and HUVECs were isolated and cultivated in vitro for further 96 h. Percentage of eGFP-positive HUVECs from samples treated with either vector with AAV9 wild-type capsids or AAV9-SLRSPPS ("SLRSPPS" disclosed as SEQ ID NO: 4) capsids was determined by FACS-analysis (in relation to untreated cells). While wtAAV9 vectors did not result in a significant transduction, AAV9 vector mutant bearing peptide motif SLRSPPS (SEQ ID No. 4) conferred transduction in 72.4+/−15.8% endothelial cells, demonstrating that AAV9-SLRSPPS ("SLRSPPS" disclosed as SEQ ID NO: 4) vectors are capable to efficiently transduce quiescent endothelial cells in human vessels in situ.

The invention claimed is:

1. A DNA polynucleotide encoding an AAV9 capsid polypeptide comprising an inserted peptide as shown in SEQ ID Nos. 1 or 6, wherein the insertion site of the peptide corresponds to amino acid 591 of the AAV9 capsid polypeptide.

2. A vector comprising the polynucleotide of claim 1.

3. A host cell comprising the polynucleotide of claim 1.

4. A method for the manufacture of a polypeptide comprising the steps of
   (a) culturing a host cell comprising the polynucleotide of claim 1; and
   (b) obtaining the polypeptide encoded by the polynucleotide or vector from the host cell.

5. A polypeptide encoded by the polynucleotide of claim 1.

6. A pharmaceutical composition comprising the polynucleotide of claim 1.

7. A pharmaceutical composition comprising the polypeptide of claim 5.

8. A method for treating or preventing a vascular disease in a subject suffering therefrom, wherein the method comprises administering to the subject a therapeutically effective amount of the polynucleotide of claim 1.

9. The method of claim 8, wherein the vascular disease is an acquired vascular disease.

10. The method of claim 8, wherein the vascular disease is an inherited vascular disease.

11. The method of claim 10, wherein the medicament is used for the prevention of inherited vascular disease.

12. A method for treating or preventing a vascular disease in a subject suffering therefrom, wherein the method comprises administering to the subject a therapeutically effective amount of the polypeptide of claim 5.

13. The method of claim 12, wherein the vascular disease is an acquired vascular disease.

14. The method of claim 12, wherein the vascular disease is an inherited vascular disease.

15. The method of claim 14, wherein the composition is used for the prevention of inherited vascular disease.

16. A method for the identification of a compound capable of binding to the polypeptide of claim 5, wherein the method comprises the steps of:
   (a) contacting the polypeptide with a target cell; and
   (b) identifying compounds bound to the polypeptide.

* * * * *

UNITED STATES PATENT AND TRADEMARK OFFICE
CERTIFICATE OF CORRECTION

PATENT NO.       : 8,476,418 B2                                    Page 1 of 1
APPLICATION NO. : 13/322121
DATED            : July 2, 2013
INVENTOR(S)      : Mueller et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 32 days.

Signed and Sealed this
Eighth Day of September, 2015

Michelle K. Lee
*Director of the United States Patent and Trademark Office*